United States Patent [19]

Van Scoik

[11] Patent Number: 5,082,667

[45] Date of Patent: Jan. 21, 1992

[54] SOLID PHARMACEUTICAL DOSAGE IN TABLET TRITURATE FORM AND METHOD OF PRODUCING SAME

[75] Inventor: Kurt G. Van Scoik, Grayslake, Ill.

[73] Assignee: Abbott Laboratories, Abbott Park, Ill.

[21] Appl. No.: 689,120

[22] Filed: Apr. 22, 1991

Related U.S. Application Data

[63] Continuation of Ser. No. 352,799, May 18, 1989, abandoned, which is a continuation-in-part of Ser. No. 203,396, Jun. 7, 1988, abandoned.

[51] Int. Cl.$^5$ ............................................. A61K 9/26
[52] U.S. Cl. .................................... 424/469; 424/470; 424/465
[58] Field of Search ............... 424/465, 469, 470, 476, 424/460, 462

[56] References Cited

U.S. PATENT DOCUMENTS

| 4,013,784 | 3/1977 | Speiser | 424/502 |
| 4,572,832 | 2/1986 | Kigasawa et al. | 424/435 |

FOREIGN PATENT DOCUMENTS

| 139460 | 5/1985 | European Pat. Off. |
| 251680 | 1/1988 | European Pat. Off. |
| 273890 | 7/1988 | European Pat. Off. |

Primary Examiner—Thurman K. Page
Assistant Examiner—Leon R. Horne
Attorney, Agent, or Firm—Steven R. Crowley

[57] ABSTRACT

A solid pharmaceutical dosage in tablet triturate form is disclosed. The tablet triturate form includes a cementatory network constituted by a water-soluble but ethanol-insoluble carbohydrate. Also included are discrete particles of a solid, water-soluble but triglyceride-insoluble active ingredient, a polymer, an emulsifier, and sodium bicarbonate wherein the discrete particles have a triglyceride coating.

21 Claims, No Drawings

5,082,667

SOLID PHARMACEUTICAL DOSAGE IN TABLET TRITURATE FORM AND METHOD OF PRODUCING SAME

This application is a continuation of U.S. Ser. No. 352,799 filed May 18, 1989, abandoned, which is a continuation-in-part of U.S. Ser. No. 203,396, filed June 7, 1988 now abandoned.

TECHNICAL FIELD

This invention relates to a specific tablet triturate suitable for oral administration of a pharmaceutically active ingredient, and in particular to a tablet triturate that dissolves relatively quickly in the buccal cavity and masks the taste of the active ingredient as well.

BACKGROUND OF THE INVENTION

Patient compliance with a prescribed regimen of taking orally administered drugs is necessary for effective treatment. However, this compliance is often adversely affected by drugs which are not palatable. Reduced compliance can also occur with a pediatric or geriatric patient who will not or cannot swallow solid tablets. Similar difficulty can occur in veterinary treatment in that animals can be uncooperative about taking the drug in tablet form.

Conventional forms of drugs for oral administration include direct compression tablets, sublingual tablets, spray congealed powders and triturate tablets. These forms, however, do not provide the advantage of the present specific tablet triturate of this invention.

Tablets which are formed by direct compression are ill suited for the rapid administration of drugs in that compressed tablets do not disintegrate or dissolve fast enough. Furthermore these tablets are difficult for certain patients to swallow.

Sublingual tablets are designed for rapid administration of medication and are placed beneath the tongue and held there until absorption of the drug has taken place through the mucous membranes. These tablets do not improve patient compliance in the above described problem areas, however. Inasmuch as the tablet is absorption in the buccal cavity, an unpalatable sensation is experienced by the patient. In the case of an infant, or psychiatric patient, the patient may also spit the tablet out.

The process of spray congealing involves cooling (or congealing) of melted substances in the form of fine particles during their travel from a spray nozzle to a distant vicinity of a spray chamber held at a temperature below the melting temperatures of the substances. If a slurry of material insoluble in the melted mass of a congealing substance is spray congealed, the insoluble material is coated with the congealing substance. This method provides taste masking. However, this process does not provide tablets for ease of oral administration of the drug. Furthermore, the congealing substance is usually a fatty acid or monoglycerides, diglycerides, or triglycerides of edible fatty acids.

Trituration is the mixing of powders using a grinding action, such as by a mortar and pestle, followed by moistening of the powders. This moistened powder is then molded into tablet form and dried. Tablets thus produced do not exhibit taste masking characteristics.

The present invention provides a solid pharmaceutical dosage in tablet triturate form which avoids the shortcomings of the prior art and is both readily dissolvable and masks the taste of the active ingredient.

SUMMARY OF THE INVENTION

The present invention contemplates a solid pharmaceutical dosage in tablet triturate form which dissolves quickly and masks the taste of the active ingredient.

This tablet triturate form includes a porous cementatory network having discrete particles encasing an active ingredient dispersed throughout the network. The network is constituted by a water soluble but ethanol insoluble carbohydrate. The discrete particles include a solid, water soluble but triglyceride insoluble active ingredient provided with a triglyceride coating.

These discrete particles are produced by first suspending the active ingredient in a melted triglyceride vehicle. The triglyceride vehicle may also contain polymers, such as polyethylene glycol (PEG); sodium bicarbonate; and emulsifiers, such as lecithin, to modify the rate and extent of drug release from the particles. This suspension is then spray congealed to form solid discrete particles having the active ingredient, polymer, sodium bicarbonate, and emulsifier all of which are encapsulated in the triglyceride vehicle.

The tablet triturate contemplated by the present invention is produced by admixing the carbohydrate, the discrete particles and a temporary liquid binder such as a water-ethanol admixture in an amount sufficient to form a damp mass. The resulting damp mass is shaped into a tablet and subsequently dried to produce the desired tablet triturate.

The present dosage form is particularly well suited for the administration of bitter tasting medication such as estazolam, clorazepate dipotassium, and the like.

Numerous other advantages and features of the present invention will become readily apparent from the following detailed description of the invention, the accompanying examples, and the appended claims.

DETAILED DESCRIPTION OF THE PREFERRED EMBODIMENTS

While this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

The present invention is directed to a solid pharmaceutical dosage in tablet triturate form. The relatively quick dissolution, acceptable taste and acceptable stability of the tablet triturate as a dosage form makes it suitable for oral administration of pharmaceutically active ingredients that have an unpleasant taste.

This tablet triturate dosage form has a porous cementatory network constituted by a water-soluble but ethanol-insoluble carbohydrate. Distributed substantially uniformly throughout the network are discrete particles of the solid, water-soluble but triglyceride-insoluble active ingredient and, where applicable, the polymer, sodium bicarbonate, and emulsifier. These particles have a triglyceride coating which is insoluble in water, ethanol, saliva or combinations thereof. As the particles are not significantly dissolved in the buccal cavity, taste masking of the active ingredient is realized. Absorption of the discrete particles occurs when they reach the digestive tract where the active ingredient is released for systemic delivery. The triglyceride coating constitutes a major portion of the weight of each discrete particle, usually about 55 to about 80 percent by weight of each discrete particle.

Suitable carbohydrates for the present purposes are monosaccharides such as fructose, dextrose and the like, disaccharides such as lactose, sucrose, and the like, as well as combinations thereof. Preferably the carbohydrate is in powder form and having a particle size distribution of less than about 100 microns in diameter. A preferred carbohydrate is lactose, more preferably lactose monohydrate.

Suitable polymers for the present purposes include PEG 200, 300, 400, 3350, and 8000, where the numerical value approximates the molecular weight. In the context of the present invention, the lower molecular weight polymers are preferred as they will produce a faster dissolution rate.

In addition to the aforementioned monosaccharides and disaccharides, a carbohydrate such as a sugar alcohol, e.g., mannitol, sorbitol, and the like, and admixtures thereof can be present in the cemetatory network in an amount up to about 20 percent by weight of the total amount of carbohydrates present.

The above identified carbohydrates form a porous cementatory network which is fast-dissolving in the buccal cavity and which serves to retain therewithin the spray congealed active ingredient or ingredients.

The active ingredients suitable for preparation of the present dosage forms are not temperature sensitive at the melting temperature of the triglyceride employed. Suitable active ingredients are those which are stable in melted and room temperature triglyceride. Illustrative such active ingredients are estazolam (8-chloro-6-phenyl -4H-s-triazolo [4,3-a][1,4] benzodiazepine), clorazepate dipotassium (7-chloro 2, 3-dihydro 2, 2-dihydroxy-5-phenyl lH-1,4-benzodiazepine 3 carboxylic acid dipotassium), and the like.

The triglyceride is a tri ester of a fatty acid and glycerol represented by the general formula $CH_2(OOCR_1)OOCR_2)CH_2(OOCR_3)$ wherein $R_1$, $R_2$, and $R_3$ are independently selected from fatty acid residues, usually of different chain lengths. These fatty acid residues are at least about $C_{16}$, preferably at least about C18 in carbon chain length. Triglycerides of this size possess a melting temperature which is satisfactory for the present purposes. Generally, illustrative triglycerides are hydrogenated vegetable oil such as hydrogenated cottonseed oil, hydrogenated animal oils, and the like. Specifically, illustrative triglycerides include tristearin and palmitodistearin. These triglycerides have good storage stability but are eventually broken down in the small intestine, thereby releasing any remaining active ingredient for systemic absorption.

Other optional ingredients that can be incorporated into the present tablet triturate dosage forms include known pharmaceutically acceptable excipients, such as flavoring, sweetening agents, and coloring agents, for example, peppermint flavor or aspartame, and the like.

The discrete particles containing the active ingredient are formed by a spray congealing process. First, a triglyceride having a melting temperature below the temperature at which the active ingredient melts is selected and converted to liquid phase by heating. If sodium bicarbonate is utilized, the sodium bicarbonate can be added to the liquid phase at this point. The active ingredient, in powder form, is then admixed with the triglyceride melt and homogeneously dispersed therein. If polymer and emulsifier are utilized, the polymer and the emulsifier can be mixed together and circulated through the system at this point. The resulting mixture is a suspension of the active ingredient, the polymer, the emulsifier, and the sodium bicarbonate in the triglyceride melt. Next, the admixture is spray congealed in a conventional manner to produce discrete particles of suitable particle size in which the active ingredient, the polymer, sodium bicarbonate, and the emulsifier are encased in a triglyceride envelope.

To produce the tablet triturate dosage form, the solid components in desired proportions are combined in a suitable vessel. A small amount of a volatizable, temporary, liquid binder having limited solubility for the carbohydrate, e.g., a water-ethanol admixture, or the like, sufficient to form a slightly damp mass of the solid components is added. This mass is then mixed to substantial homogeneity. The produced homogeneous mass is forced into a mold having tablet shaped holes in a plate. The tablets are solidified by evaporating the volatizable liquid binder present, thereby yielding the porous tablet triturate dosage forms of the present invention. These tablet triturates have a rigid self-supporting structure.

When this tablet triturate is inserted in the buccal cavity, the carbohydrate cementatory network of the present tablet triturate is readily and rapidly dissolved in approximately 5 seconds by the saliva present in the buccal cavity. However, the discrete particles containing the active ingredient are substantially unaffected by the saliva but can be readily swallowed without the taste of the encapsulated active ingredients becoming manifest to the patient.

In the dosage form of the present invention, the weight ratio of carbohydrate:discrete particles preferably is in the range of about 4:1 to about 100:1. The discrete particles can constitute about 1 percent to about 25 percent by weight of the dosage form.

The weight ratio of active ingredient:triglyceride is in the range of about 1:1 to about 1:5, preferably about 1:2 to about 1:4.

The particle size of the active ingredient usually is in the range of about 75 microns to about 150 microns (preferably about 100 microns to about 150 microns in diameter).

The maximum particle size of the discrete particles is such that the discrete particles are not discernible by a patient when they are present in the buccal cavity. A sensation of grittiness or sandiness is thereby avoided. Suitable discrete particle sizes are preferably less than about 180 microns in diameter.

A ratio of liquid binder to dry solid components which is sufficient to yield a damp homogeneous mass is about 10-15:100 (v/m), respectively.

The shape of the tablet triturate is not critical to the performance of the tablet. Standard manufacturing and handling, as well as administration considerations determine the ultimate shape of the tablet.

The following examples further illustrate a dosage form of the present invention as well as a method of making the same; however, this example is not to be construed as a limitation of this invention.

EXAMPLE 1

The water-soluble but triglyceride-insoluble active ingredient utilized is crystalline estazolam. The triglyceride utilized is hydrogenated cottonseed oil.

The cottonseed oil, in solid flake form, is placed in a stainless steel vessel and heated to a temperature in the range of about 62° to about 66° C. Sufficient heat is supplied to melt the oil. The temperature of the molten oil is maintained above the melting temperature of the oil but below the melting temperature of estazolam. Estazolam in powder form is added to the molten oil in the vessel while maintaining vigorous agitation. A commercially available homogenizer is used as an agitator to ensure suspension and distribution of estazolam crystals substantially uniformly throughout the oil. The estazolam particle size is in a range of about 75 to about 150 microns in diameter.

To ensure satisfactory coating of the estazolam, the weight ratio of estazolam:cottonseed oil in the produced suspension is about 1:4.

After the estazolam is adequately distributed into the molten oil, the resulting suspension is pumped from the vessel using a sanitary food-grade pump through heated hoses to a spray gun located inside of a fluid-bed dryer. The spray gun and the air feed to the spray gun are also heated to prevent solidification of the molten suspension during this stage of the manufacturing process. As the molten suspension is forced through the spray gun, a liquid suspension stream is broken up into fine droplets by the heated atomizing air which droplets consist essentially of crystals of estazolam enclosed in the hydrogenated cottonseed oil droplet. These droplets contact cool air drawn into the fluid bed dryer and solidify as discrete particles. The discrete particles are then collected from the bottom of the fluid-bed dryer as a free flowing powder which is colorless to off-white in color. This material is then classified into desired particle size ranges, e.g., smaller than 80 mesh (about 177 microns in diameter), using pharmaceutical sieves. Discrete particles having a relatively narrow particle size distribution in the range of about 80 to about 175 microns are selected for incorporation into the dosage forms.

To manufacture the tablet triturate dosage form, lactose monohydrate is combined with various flavor and/or sweetening agents along with the produced discrete particles. All components are in powder form. An illustrative composition is presented in TABLE I, below.

TABLE I

| Composition of a Tablet Triturate Form | |
|---|---|
| Component | Weight, mg |
| Discrete particles* | 10 |
| Lactose monohydrate | 85 |
| Sweetening agent | 3 |
| Flavoring agent | 2 |

*The composition of the discrete particles is estazolam:hydrogenated cottonseed oil in a weight ratio of about 1:4.

The foregoing components are admixed in a suitable vessel. A relatively small amount of a temporary liquid binder, sufficient to dampen the admixture and form a damp mass is added. The liquid binder utilized in this instance is a 60:40 (v/v) admixture of ethanol USP:distilled water. However, the ethanol/water liquid binder may be adjusted to other proportions, or may be comprised of water alone. The amount of liquid binder utilized was 14 milliliters for 100 grams of dry components.

The formed damp mass is next placed in tablet shaped holes in a stainless steel plate to mold tablets. The molded tablets are then removed from the plate and dried.

Machines suitable for manufacturing the tablet triturate dosage form of the present invention are commercially available, inter alia, from Vector-Colton Inc., Marion, Iowa.

EXAMPLE 2

Cottonseed oil is heated as described in Example 1. Sodium bicarbonate and estazolam are added to the molten oil in the vessel while vigorous agitation is maintained as previously described. PEG 300 and lecithin are mixed together and added to the molten suspension. The resulting suspension is thereafter processed as described in Example 1.

The composition of the discrete particles is illustrated in Table II below. In this case, the composition of the discrete particles is calculated to be 25 percent estazolam.

TABLE II

| Composition of Discrete Particles | |
|---|---|
| Component | Weight, mg. |
| estazolam | 25 |
| sodium bicarbonate | 7.5 |
| lecithin | 10 |
| hydrogenated cottonseed oil | 52.5 |
| PEG 300* | 5 |

*PEG 300 is available from Union Carbide

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

I claim:

1. A solid pharmaceutical dosage in tablet triturate form which rapidly dissolves upon oral administration, said tablet comprising a tablet matrix comprising a water-soluble but ethanol-insoluble carbohydrate wherein the carbohydrate is a monosaccharide, a dissaccharide or a combination thereof, said tablet also comprising discrete particles of a solid, water-soluble but triglyceride-insoluble active ingredient, said particles having a triglyceride coating which is insoluble in water, ethanol, saliva or combinations thereof wherein the triglyceride is a triester of glycerol wherein the esters are derived from fatty acids independently selected from fatty acids having at least 16 carbon atoms, said triglyceride-coated particles of active ingredient comprising from about 50% to about 80% by weight of triglyceride, and wherein the weight ratio of carbohydrate to discrete particles of triglyceride-coated active ingredient is from about 4:1 to about 100:1 and wherein said triglyceride-coated particles are distributed throughout the tablet matrix.

2. The dosage form in accordance with claim 1 wherein the active ingredient is estazolam.

3. The dosage form in accordance with claim 2 wherein the discrete particles further comprise an emulsifier and a polymer.

4. The dosage form in accordance with claim 3 wherein the discrete particles further comprise sodium bicarbonate.

5. The dosage form in accordance with claim 1 wherein the tablet matrix comprises lactose and said discrete particles comprise estazolam coated with hydrogenated cottonseed oil.

6. The dosage form in accordance with claim 1 wherein the discrete coated particles comprise from about 1 percent to about 25 percent by weight of the dosage form.

7. The dosage form in accordance with claim 3 wherein the carbohydrate is lactose, the active ingredient is estazolam, the triglyceride is hydrogenated cottonseed oil, the polymer is polyethylene glycol of molecular weight 300, and the emulsifier is lecithin, wherein the carbohydrate comprises from about 80 to about 99 percent of the total weight of the tablet.

8. The dosage form in accordance with claim 1 wherein the triglyceride coating masks the taste of the active ingredient.

9. The dosage form in accordance with claim 1 wherein the triglyceride is hydrogenated cottonseed oil.

10. The dosage form in accordance with claim 3 wherein the polymer is polyethylene glycol.

11. The dosage form in accordance with claim 10 wherein the polyethylene glycol has a molecular weight of from about 200 to about 8000.

12. The dosage form in accordance with claim 3 wherein the emulsifier is lecithin.

13. The dosage form in accordance with claim 1 wherein the carbohydrate is lactose.

14. A solid pharmaceutical dosage in tablet triturate form which rapidly dissolves upon oral administration, said tablet comprising a tablet matrix comprising a water-soluble but ethanol-insoluble carbohydrate wherein the carbohydrate is a monosaccharide, a disaccharide or a combination thereof, said tablet also comprising discrete particles of a solid, water-soluble but triglyceride-insoluble active ingredient, polyethylene glycol, sodium bicarbonate and an emulsifier, said particles having a triglyceride coating which is insoluble in water, ethanol, saliva or combinations thereof, wherein the triglyceride is a triester of glycerol wherein the esters are derived from fatty acids independently selected from fatty acids having at least 16 carbon atoms, said triglyceride-coated particles of active ingredient comprising from about 50% to about 80% by weight of triglyceride, and wherein the weight ratio of carbohydrate to discrete particles of triglyceride-coated active ingredient is from about 4:1 to about 100:1 and wherein said triglyceride-coated particles are distributed throughout the tablet matrix.

15. The dosage form in accordance with claim 14 wherein the triglyceride coating masks the taste of the active ingredient.

16. The dosage form in accordance with claim 14 wherein the triglyceride is hydrogenated cottonseed oil.

17. The dosage form in accordance with claim 14 wherein the polyethylene glycol has a molecular weight of from about 200 to about 8000.

18. The dosage form in accordance with claim 14 wherein the emulsifier is lecithin.

19. The dosage form in accordance with claim 14 wherein the carbohydrate is lactose.

20. The dosage form in accordance with claim 14 wherein the active ingredient is estazolam.

21. A solid pharmaceutical dosage in tablet triturate form which rapidly dissolves upon oral administration, comprising discrete particles comprising estazolam, polyethylene glycol of molecular weight 300, sodium bicarbonate and lecithin in a weight ratio of about 5:1:1.5:2, said particles having a hydrogenated cottonseed oil coating wherein the hydrogenated cottonseed oil coating comprises about 50% by weight of the coated particles, said coated particles being distributed throughout a tablet matrix comprising lactose monohydrate wherein the weight ratio of lactose monohydrate to coated particles is about 8.5 to 1.

* * * * *